(12) United States Patent
Maziere et al.

(10) Patent No.: US 6,228,890 B1
(45) Date of Patent: *May 8, 2001

(54) USE OF ALICYCLIC DIAMINES AS IMMUNOMODULATORS

(75) Inventors: Jean-Claude Maziere, Amiens; Amar Achour, Creteil; Jean-Charles Landureau, Villenoy; Daniel Zagury, Paris, all of (FR)

(73) Assignee: Neovacs, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/011,145
(22) PCT Filed: Aug. 2, 1996
(86) PCT No.: PCT/FR96/01242
  § 371 Date: Jun. 3, 1998
  § 102(e) Date: Jun. 3, 1998
(87) PCT Pub. No.: WO97/05859
  PCT Pub. Date: Feb. 20, 1997

(30) Foreign Application Priority Data

Aug. 3, 1995 (FR) .................................................. 95 09459

(51) Int. Cl.$^7$ ...................................................... A61K 31/13
(52) U.S. Cl. ........................... 514/659; 514/660; 514/661
(58) Field of Search ................................... 514/659, 660, 514/661

(56) References Cited

U.S. PATENT DOCUMENTS 3,244,750 * 4/1966 Humber ............................... 260/563
4,060,639 * 11/1977 Jacobus et al. ........................ 424/325
5,116,823 * 5/1992 Calabresi et al. ........................ 514/50

FOREIGN PATENT DOCUMENTS

1387971 * 12/1965 (FR).

OTHER PUBLICATIONS

Popp et al 67 CA: 53793a, 1967.*

Elwell et al 106 CA:135100k, 1987.*

Science, vol. 270, Dec. 15, 1995, pp. 1811–1815, XP000616644. Cocchi, F. et al., "Identification of Rantes, MIP–1alpha, and MIP–1beta as the major HIV–suppressive factors produced by CD8+ T cells."

* cited by examiner

Primary Examiner—Russell Travers
(74) Attorney, Agent, or Firm—Browdy and Neimark

(57) ABSTRACT

The invention discloses the use of a compound of general structural formula (I) R-NH-K-Q-K-NH-R, wherein Q is a divalent radical of formulae (II) to (V), K is a methylene group, or, when Q is a group of formula (II), K is a binding valency. R is a radical selected from the group comprising benzyl, benzyl substituted with halogen or trihalomethyl groups, substituted trihalomethyl benzyl, indanyl, alkyl, cycloalkyl, cycloalkylalkyl, alkenyl, cycloalkenylalkyl, bicycloalkyl, bicycloalkenylalkyl, bicycloalkylalkyl; and the organic or mineral acid addition salts thereof. The preparation of a medicament for correcting the expression of cytokine genes and/or a receptor thereof for treating a dysfunction related to an exogenous or endogenous disease state is also described.

14 Claims, 8 Drawing Sheets

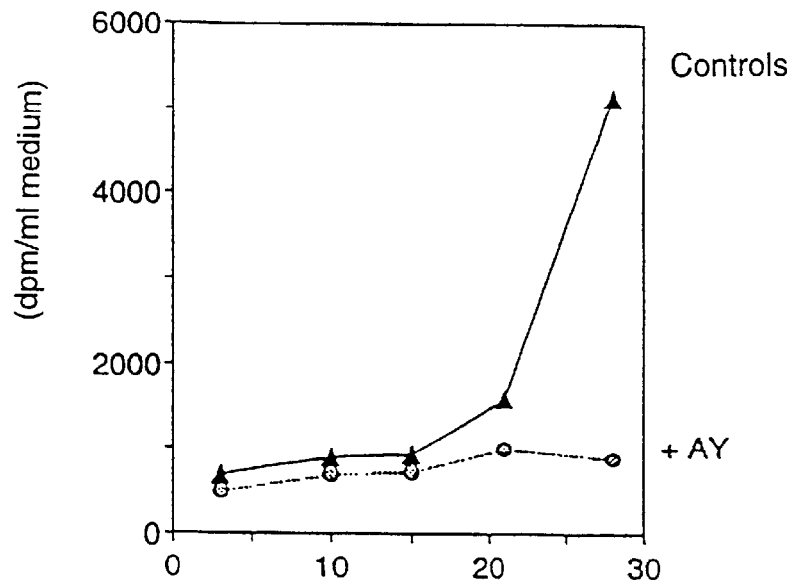
(d)   Fig.3
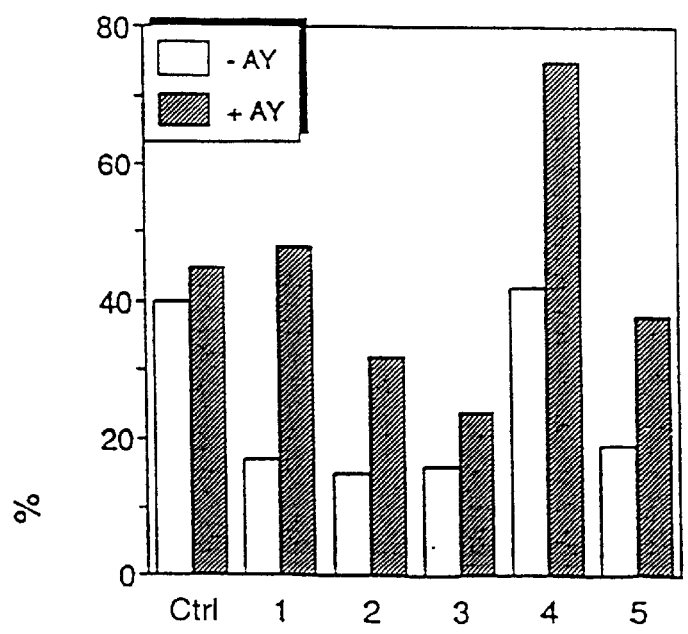
Fig.4

USE OF ALICYCLIC DIAMINES AS IMMUNOMODULATORS

The present invention relates to novel uses for alicyclic diamines.

FR-A-1 387 971 describes novel alicyclic diamines and a process for the preparation thereof.

Alicyclic diamines represented by a formula with general structure:

R-NH-K-Q-K-NH-R  (I)

where Q represents a divalent radical with the following formulae II to V:

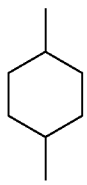  (II)

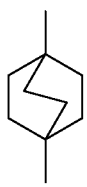  (III)

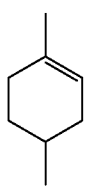  (IV)

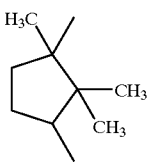  (V)

K represents a methylene group or, when the symbol Q is represented by formula II, a valence bond and the symbol R is a radical selected from the group formed by the following radicals VI to XVII:

VI Benzyl;
VII Benzyl substituted by one, two or three trihalomethyl groups;
VIII Substituted trihalomethyl benzyl;
IX Indanyl;
X Alkyl;
XI Cycloalkyl;
XII Cycloalkylalkyl;
XIII Alkenyl;
XIV Cycloalkenylalkyl;
XV Bicycloalkyl;
XVI Bicycloalkenylalkyl;
XII Bicycloalkylalkyl;

and their addition salts with mineral or organic acids, have properties which affect lipid metabolism.

After a great deal of research, the applicant has discovered that the products defined above have remarkable, original immunomodulating properties.

In particular, the above products are capable of restoring expression of cytokine genes and/or their receptor in the event of a dysfunction of such genes connected with an exogenous or endogenous pathology. These properties are illustrated in the experimental section below.

They can also stimulate the production of inflammatory molecules which are essential for defending the human organism, such as chimiokines (MIP1 α, β, and Rantes, the antiviral properties of which have been described, for example, by Cocchi et al., Science, 270, 1811–1518, 1995).

Diamines with formula I appear to act as a stimulator for type TH1 cytokines which are known to be greatly disturbed in AIDS ($IL_2$, $IL_{12}$, for example); the apoptosis effect induced by HIV and other pathologies could be limited by this mechanism.

For this reason, the present invention concerns the use of a compound with formula I as defined above for preparing an immunomodulating drug, which is in particular capable of modulating the expression of cytokine genes and/or their receptor in the event of a dysfunction connected with an exogenous or endogenous pathology, and for stimulating cytokine production.

This pathology could be connected with a viral infection such as type I or type II AIDS, herpes, hepatitis, papilloma, or to a parasitic infection such as leishmaniosis, malaria or bilharziosis. It can also be of iatrogenic origin, for example, induced by the action of immunosuppressors such as cyclosporin or by the action of corticoids or by a tumor, in particular a haematological tumor such as myeloma or a tissue tumor.

In particular, the pathology concerned is an autoimmune disease such as rheumatoid polyarthritis, lupus erythematosus or autoimmune diabetes.

A more detailed definition of compounds with formula I above and a process for the preparation thereof and known applications is given, for example, in FR-A-1 387 971 and its French and foreign equivalents, in particular French special drug patent N° 3559 M. There is also a great deal of literature concerning these compounds, in particular trans-1,4-bis [2-chlorobenzylaminomethyl] cyclohexane dihydrochloride, also known as AY 9944.

In particular, data relating to the pharmacology and toxicology of this product have been widely described in the literature.

The present invention particularly concerns the use of a compound as above for preparing a drug for the treatment of:
a viral disease;
a parasitic disease;
an iatrogenic disease;
a tumor;
an autoimmune disease.

For these uses in particular, a compound with formula I is used in which the symbol Q represents a 1,4-cyclohexanediyl radical, i.e. where the symbol Q corresponds to the above formula II, in particular a compound with formula I in which the symbol R is a benzyl radical or a benzyl radical substituted with a halogen such as fluorine, bromine and in particular chlorine, or by one, two or three trihalomethyl groups, or by a trihalomethyl benzyl radical substituted with one or more, for example one, two or three halogens or $C_1$–$C_5$ alkyl or alkoxy radicals, and more particularly the compound AY 9944, namely the dihydrochloride of the compound with formula:

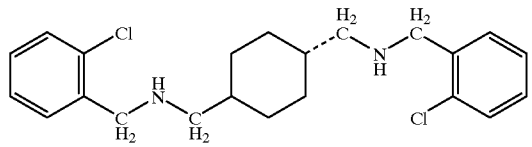

These properties of restoring expression of cytokine genes and/or their receptor in the event of a dysfunction of these genes connected with an exogenous or endogenous pathology, which are illustrated below in the experimental section, justify the use of derivatives with formula I described above and salts thereof as a drug for correcting the expression of cytokine genes and/or their receptor in the event of a dysfunction connected with an exogenous or endogenous pathology.

The drugs of the present invention can be used, for example, for curative or preventative treatment of the pathologies listed above.

They are of particular use in the treatment of autoimmune diseases.

The usual dose, which varies depending on the subject treated and the affliction under consideration, can be 10 mg to 2 g per day, orally in man, of the compound known as AY 9944, for example, as required.

As a drug, the above compounds with formula I and the salts thereof can be incorporated into pharmaceutical compositions for digestive or parenteral administration. These pharmaceutical compositions can be solids or liquids, for example, in pharmaceutical forms which are routinely used in human medicine, such as simple or sugar-coated tablets, capsules, granules, syrups, suppositories, or injectable preparations; they are prepared using the normal methods. The active ingredient or ingredients can be incorporated with excipients which are normally used in these pharmaceutical compositions, such as talc, gum arabic, lactose, starch, magnesium stearate, cocoa butter, aqueous or non aqueous vehicles, animal or vegetable fats, paraffin derivatives, glycols, various wetting agents, dispersing agents or emulsifiers, and preservatives.

We have also discovered that when an immunomodulating compound with formula I as defined above is combined with a compound with anti-viral properties, such as DDI, DDC, antiproteases, 3TC and, preferably, AZT, their respective effects are potentiated as illustrated below in the experimental section.

For this reason, the present application also concerns a combination characterized in that it comprises a compound as defined above, in particular trans-1,4-bis [2-chlorobenzylaminomethyl] cyclohexane dihydrochloride and a compound with anti-viral properties.

The antiviral compound is preferably selected from DDI, DDC, antiproteases, 3TC and, in particular, AZT.

BRIEF DESCRIPTION OF THE FIGURES

FIG. 3 shows the effect of AY 9944 in a concentration of $3 \times 10^{-6}$ M on the RT activity found in the medium as a function of culture time.

FIG. 4 shows the effect of AY 9944 in a concentration of $3 \times 10^{-6}$ M on the percentage of cells expressing the IL-2 receptor in populations of lymphocytes in peripheral blood isolated from a healthy subject (control: Ctrl) and various patients with AIDS (1 to 5).

The following examples illustrate the present invention.

EXPERIMENTAL SECTION

Mono-nuclear cells from subjects with AIDS were isolated over a Ficoll gradient and activated with phytohemagglutinin (PHA) overnight at 37° C. They were then washed and cultured to $8 \times 10^5$/ml in RPMI medium supplemented with 10% decomplemented foetal calf serum in the presence of 40 UI/ml of interleukin-2 (recombinant, Roussel-Uclaf) and in the presence or otherwise of AY 9944 at the tested concentration, namely $3 \times 10^{-6}$ M. The cellular viability (Trypan Blue test) was counted and monitored every 3 days with or without treatment using the tested product or products and the medium was renewed.

Cell typing was carried out periodically using a cell sorter ("FACS", Beckton-Dickinson) using monoclonal antibodies conjugated to fluorescein generated against membrane CD4 antigen characteristic of auxiliary T lymphocytes.

Example 1

Effect of cellular proliferation on percentage viability

Figure 1:
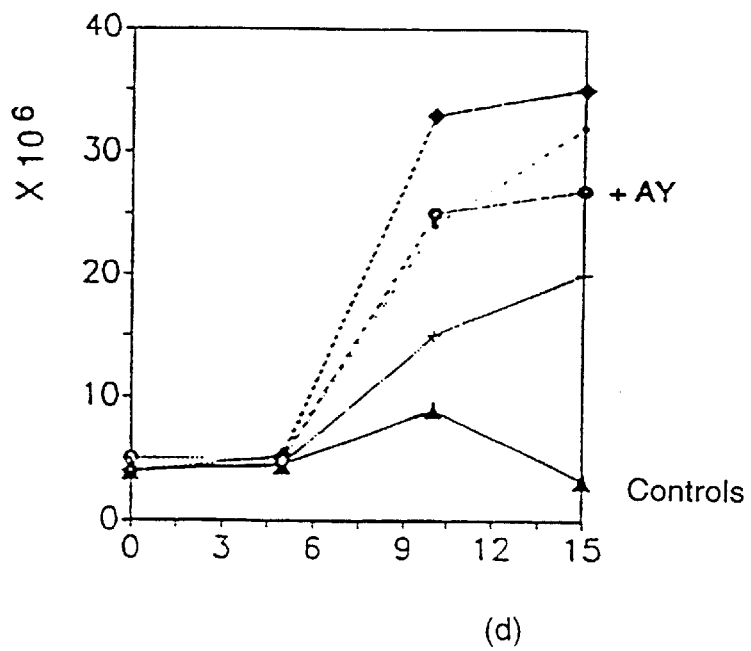
FIG. 1 shows the effect of AY 9944 (AY) in a final concentration of $3 \times 10^{-6}$ M on the number of mono-nuclear cells present in a culture of peripheral blood from a subject with AIDS (T4=400/mm$^3$). The culture time in days in along the abscissa axis and the number of cells per well is up the ordinate axis.

FIG. 1 shows that while the number of mono-nuclear cells present in the blood from a donor with AIDS (T4: 400/mm$^3$) increased little, then decreased after 10 days (cytopathogenic effect of virus and apoptose process) in infected cells (controls), in contrast a spectacular proliferation was observed in infected cultures which had been treated with the tested molecules (AY: AY 9944) at a concentration of $3 \times 10^{-6}$ M. Thus for AY 9944, for example, the number of cells after 15 days of culture was 5 to 7 times that of untreated cultures.

Figure 2:
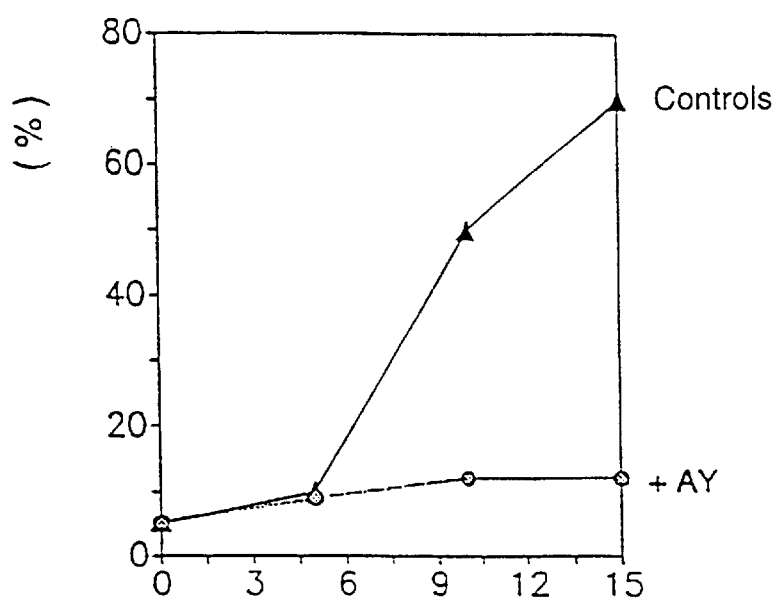
FIG. 2 shows the effect of AY 9944 in a concentration of $3 \times 10^{-6}$ M on the percentage of viable cells in a culture of peripheral blood from a subject with AIDS (T4=400/mm$^3$). The culture time in days is along the abscissa axis and the percent cellular mortality is up the ordinate axis.

Further, FIG. 2 shows that, for example in the case of cultures treated with AY 9944, the percentage of dead cells in the culture was maintained after infection at around 10% but reached about 70% two weeks after infection in the case of infected but untreated cultures (controls). Further, as it is known that these cells die by apoptosis induced by the AIDS virus, it can be concluded that AY 9944 has an anti-apoptogenic effect. This anti-apoptogenic effect is corroborated by the results of trials on cytokines given below.

Thus the presence of a compound with formula (I) in the culture medium protects the mono-nuclear cells from the cytopathogenic effect of the virus and allows considerable proliferation in the presence of lectin (PHA).

Example 2

Effect on reverse transcriptase (RT) activity found in the culture medium

The reverse transcriptase (RT) activity was measured as described by Barré-Sinoussi & al. (Science, 1983, 220:868). The RT activity was measured in a culture medium of infected cells at different culture times.

The results shown in FIG. 3 clearly demonstrate that the RT activity found in the medium remained extremely low in the event of cultures treated with AY 9944 but increased by more than 1000% in the supernatant fluids of untreated cultures. This spectacular effect suggests that this type of compound drastically reduces the viral charge. Further, it will be shown below that this is not due to direct inhibition of the (RT) enzyme but to inhibition of viral production by other mechanisms.

Example 3

Effect on expression of interleukin 2 (IL-2) receptors

Interleukin 2 is a cytokine which plays a fundamental role in regulating the immune system, in particular the multiplication of auxiliary T lymphocytes, which are known to be particularly affected in AIDS. FIG. 4 shows particularly clear stimulation of the expression of the IL-2 receptor in cultures treated with AY 9944. Note that this study was carried out on peripheral blood lymphocytes from 5 different patients and in all cases a large increase in IL-2 receptor was observed, including in patient n°4 in whom the degree of expression of the receptor was not significantly reduced. In the latter case, there was thus an over-expression of the IL-2 receptor with respect to the control (peripheral blood lymphocytes from a normal subject). For patients 1, 2 and 5 the percentage receptor expression went from 15–18% (as opposed to 40% in the control) to 30–45%, i.e. there was a genuine normalization in the degree of expression of this receptor. Finally, note that the tested compound had no notable effect on the peripheral blood lymphocytes in a healthy patient (control).

This effect is very important; IL-2 is considered to be one of the cytokines which plays a major role in immunity and dysregulation of its production can be one of the key points in problems observed following HIV infection. The drop in the number of IL-2 receptors correlates well with the CD4 count and the viral charge. Recent experiments have also shown that the early stage expression viral protein Tat inhibits expression of the IL-2 messenger (Chirmule & al. 1995, J.Virol. 69: 492).

Example 4

Effect on the percentage of cells expressing CD4

Figure 5:
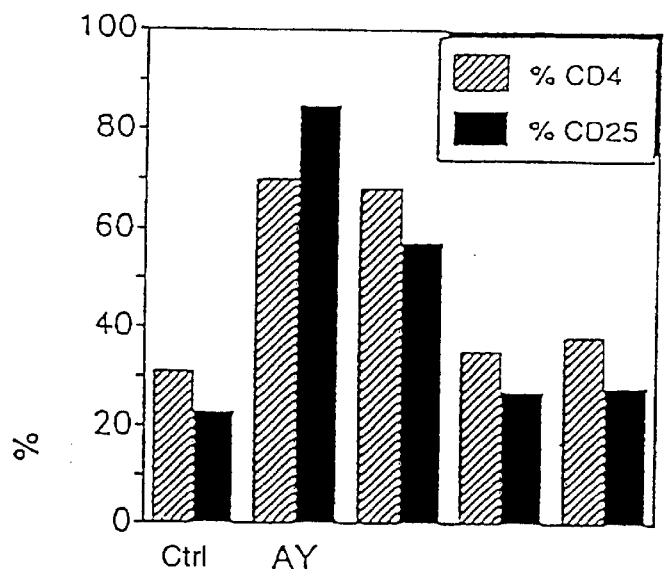
FIG. 5 shows the effect of a certain number of tested products at a concentration of $3 \times 10^{-6}$ M on the percentage of peripheral blood lymphocytes expressing CD4. The control represents untreated peripheral blood lymphocytes from subjects with AIDS (T4 about 400/mm$^3$).

It is known that a reduction in the number of T4 lymphocytes expressing the marker CD4 is one of the most clear characteristics of AIDS infection, with the result that counting "CD4" has become one of the most widely used parameters for following the development of the disease. FIG. 5 shows a considerable rise in the percentage of cells expressing CD4 (detected by FACS using a fluorescent antibody generated against CD4). In this series of experiments, AY 9944 (AY) proved to be the most effective, causing the percentage of CD4+ cells to rise by about 30% in the control (untreated peripheral blood lymphocytes in a sick subject) to about 70% for peripheral blood lymphocytes cultivated in the presence of the two products cited above.

In summary, after treatment with AY 9944 a positive effect was observed on cellular proliferation and on cellular viability, a reduction in the viral charge, a stimulation in the expression of interleukin 2 messengers and the Tac receptor of interleukin 2, and finally an increase in the percentage of CD4+ lymphocytes with re-establishment of the normal CD4/CD8 ratio. Note that similar results were obtained when the tested product was used at a concentration of $10^{-7}$ M or $10^{-8}$ M.

Example 5

Effect on transcriptional level

The effect of AY 9944 was studied on the expression of messenger RNA of IL-12, an interleukin which plays an equally important role in T lymphocyte proliferation and is secreted by cells presenting antigens. $10^6$ cells were lysed, the DNA extracted using conventional techniques, the corresponding RNAs obtained using commercially available reverse transcriptase and then amplified by PCR using primers corresponding to the desired RNA. The results show that AY 9944 increases the expression of messenger RNA coding for IL-12. The PCR technique was carried out using two different primers with formulae:

TL 12 - P35 (+) 5' CAT GCT TTC AGA ATT CGG GC 3'
TL 12 - P35 (−) 5' GTT AGC TCA GAT GCT TTC ATG 3'
TL 12 - P 40 (+) 5' CCC TGA CAC CTG GAG TAC TC 3'
TL 12 - P 40 (−) 5' GGC TAT ACC ATG AAG CCT AG 3' corresponding to two sub-units of IL-12 (P40: lines 1 to 4; P35: lines 5 to 8). The mRNAs of glyceraldehyde 3 phosphate dehydrogenase (GAPDH) were studied as a reference (lines 9 to 12).

It appears that the tested product acts on a transcriptional level, among other mechanisms, re-establishing the expression of certain genes which have been repressed by retroviruses such as HIV-1. Action is thus observed prior to early stage perturbations induced in the genome by pathogenic agents.

Example 6

Effect on cellular differentiation

Other experiments were carried out with the aim of studying the effect of AY 9944 on differentiation of mono-nuclear cells. After 6 days of culture in the presence of AY 9944, a substantial increase was observed in the percentage of activated macrophages in a population of mono-nuclear cells obtained from peripheral blood of a subject with AIDS.

Example 7

Effect on reverse transcriptase measured in vitro (acellular extract)

Figure 6:
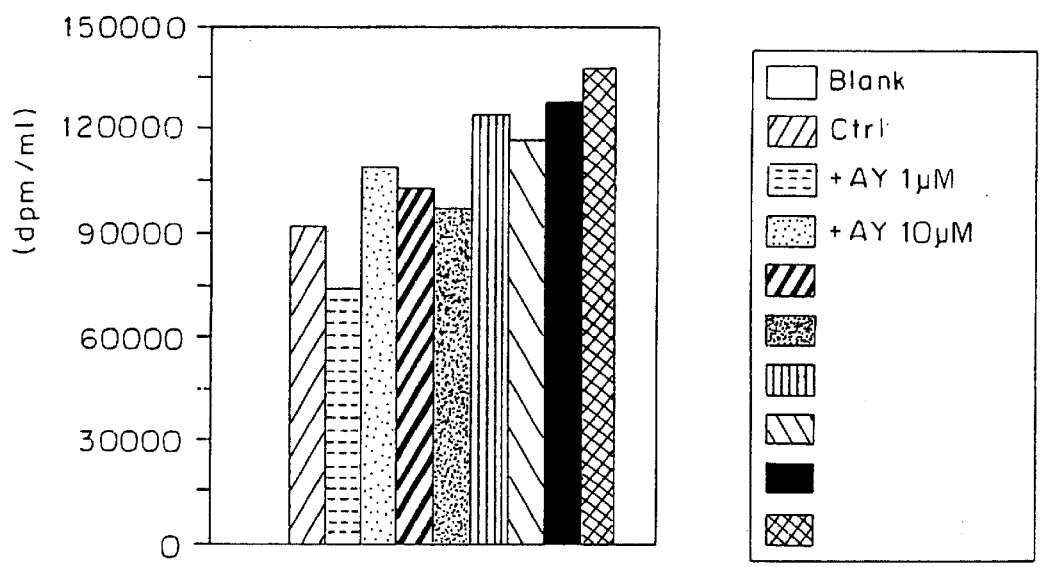
FIG. 6 shows the effect of tested products on the reverse transcriptase activity measured on an acellular extract obtained from mono-nuclear cells in a subject with AIDS.

It was also shown that the reduction in RT activity in the supernatant fluids of cultures treated with AY 9944 (see FIG. 3) was not due to a direct inhibiting effect of the product. FIG. 6 shows that, for acellular extracts, none of the tested agents significantly inhibited RT activity in the range of concentrations used ($10^{-6}$ to $10^{-5}$ M).

The results obtained with AY 9944 are shown in the third and fourth columns from the left, the other columns on the right corresponding to other tested products.

In conclusion, compounds with formula (I) are not inhibitors of reverse transcriptase. This confirms the original nature of their activity, said compounds not having a common point of action with current AZT type drugs.

Example 8

Figure 7:
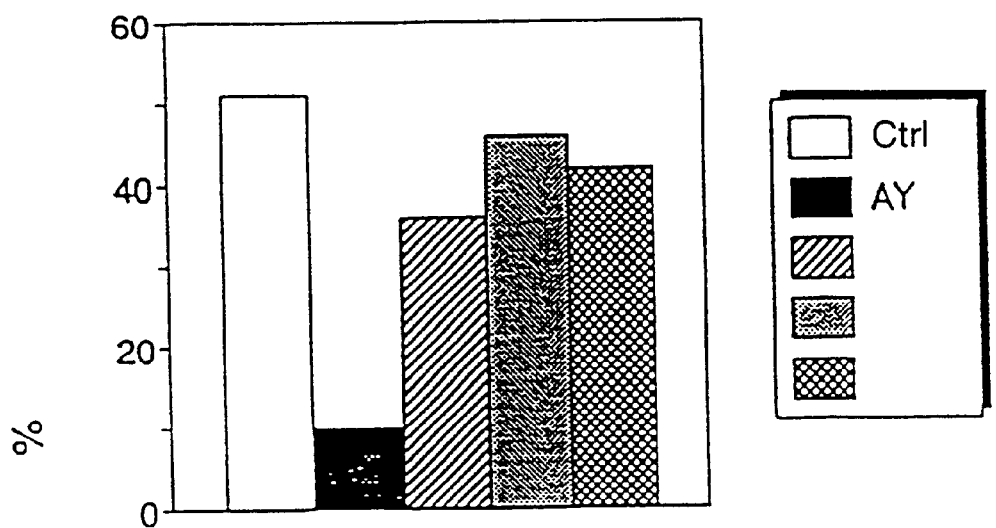
FIG. 7 shows the effect of tested products in a dose of $3 \times 10^{-6}$ M against the cytopathogenic effect of HIV-1 III B virus against lymphocytes obtained from a healthy subject.
Figure 8:
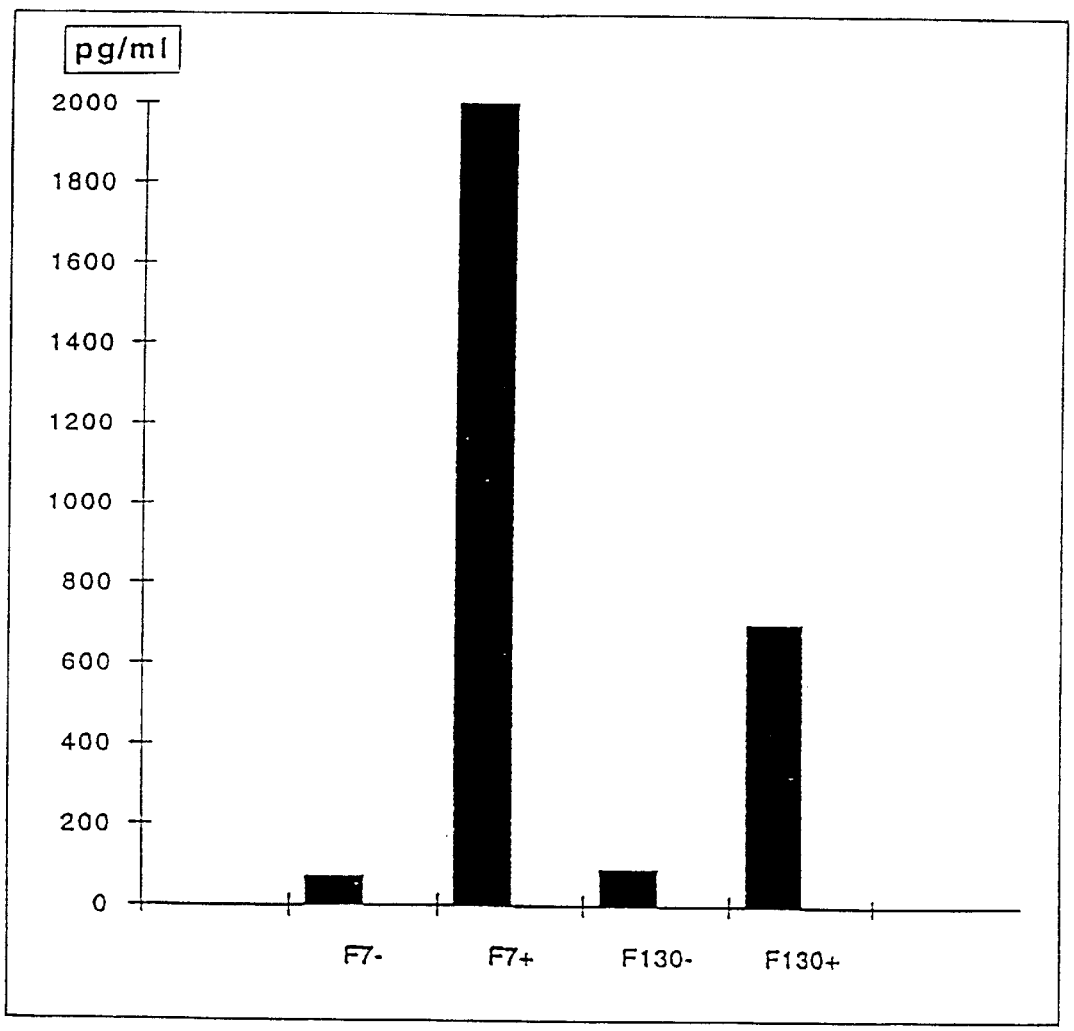
FIGS. 8, 9, 10 and 11 show the effect of tested products in a dose of $3 \times 10^{-6}$ M on cytokine synthesis, respectively IFN γ, MIP1α, MIP1β, and Rantes.
Figure 9:
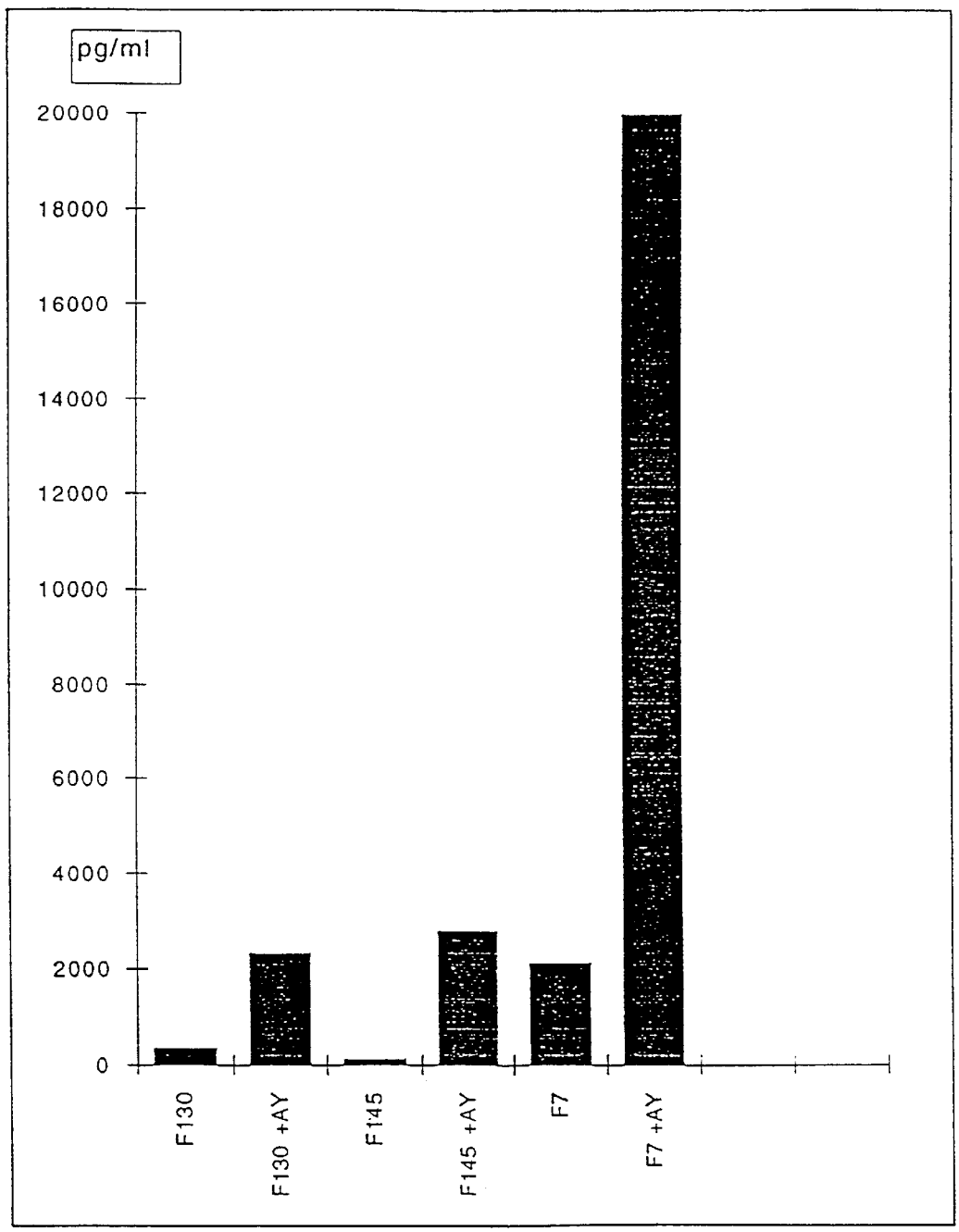
Figure 10:
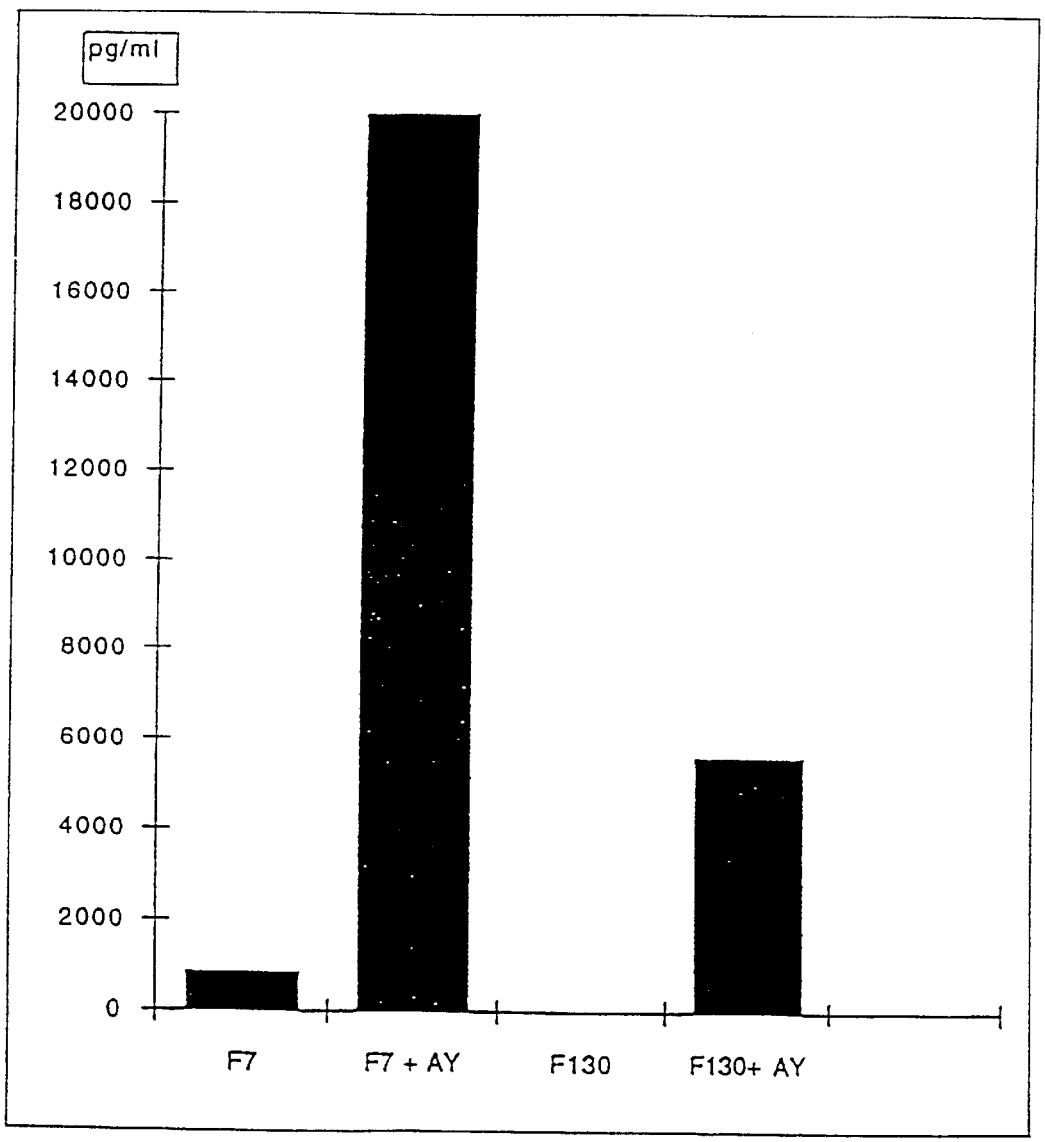
Figure 11:
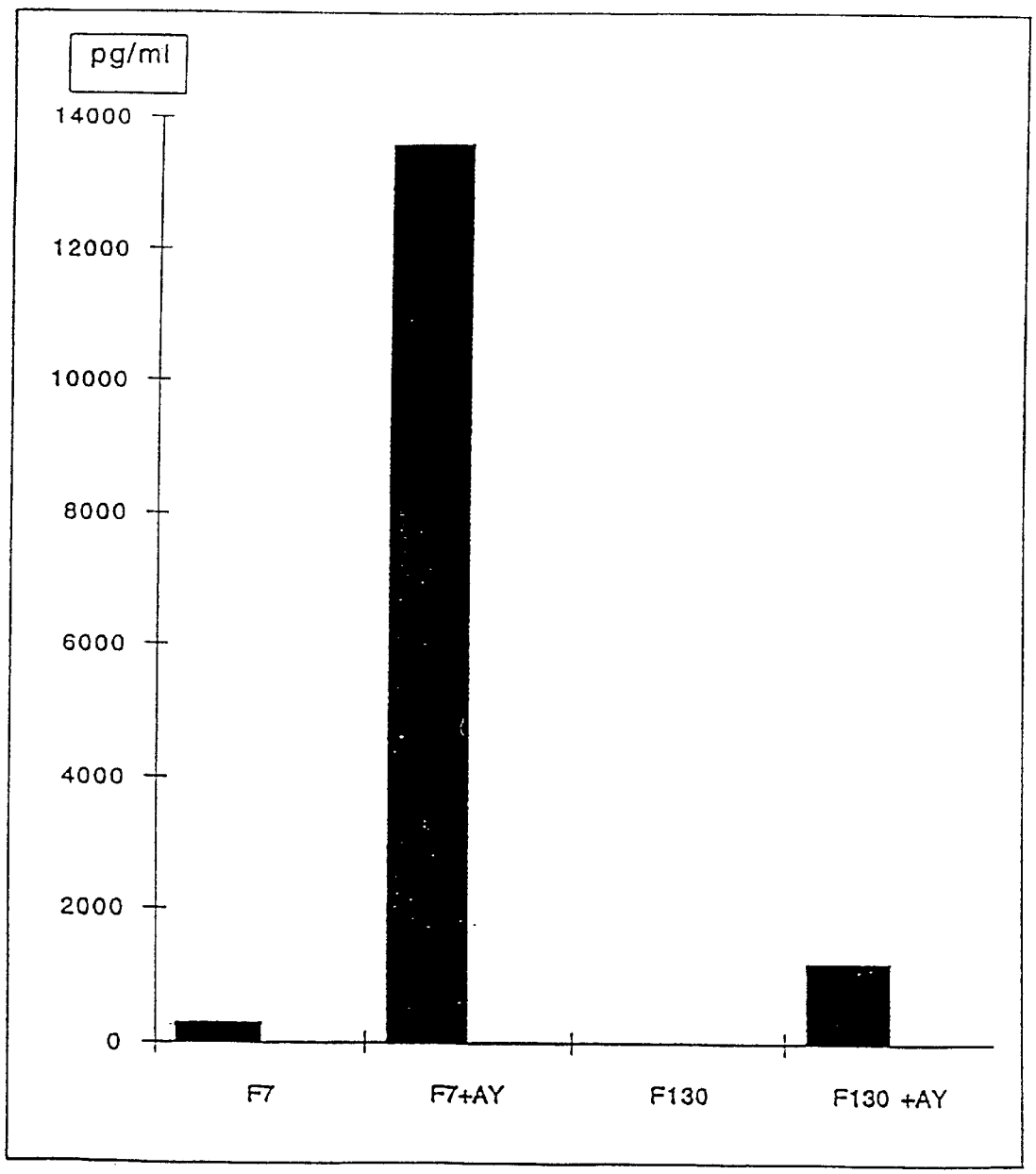

In vitro protection against infection by HIV of lymphocytes treated with amphiphilic cationic molecules Lymphocytes from the peripheral blood of a healthy individual were used, secondarily infected in vitro with a particularly virulent strain (HIV-IIIB) so as to monitor the effect of the tested products against a high viral charge. FIG. 7 shows that, in this case, in the cells which had been pre-treated with the products ($3 \times 10^{-6}$ M of tested product) for a week before in vitro infection, AY 9944 protected the cells from the cytopathogenic effect of the virus.

Examples 9 to 12

Mono-nuclear cells from subjects with AIDS were isolated over a Ficoll gradient and activated with phytohemagglutinin (PHA) overnight at 37° C. They were then washed and cultured to $8 \times 10^5$/ml in RPMI medium supplemented with 10% decomplemented foetal calf serum in the presence of 40 UI/ml of interleukin-2 (recombinant, Roussel-Uclaf) and in the presence or otherwise of AY 9944 at the test concentration, namely $3 \times 10^{-6}$ M. The cellular viability (Trypan Blue test) was counted and monitored every 3 days with or without treatment using the tested product or products and the medium was renewed.

On the $10^{th}$ day, the quantities of IFN γ, MIP1α, MIP1β and Rantes produced in the culture medium were measured. The results are shown in FIGS. 8, 9, 10 and 11. The two columns on the left correspond to one patient (F7) and the other columns to another patient (F130). For each patient, the lefthand column (−) represents production without AY 9944 and the righthand column (+) represents production with AY 9944.

In all cases, cytokine synthesis was considerably increased in the presence of AY 9944 and their production was maintained at a high level during the four weeks of culture.

Example 13

Synergy between AY 9944 and an anti-viral compound

H9 human cell line cells were infected with the viral strain HIV-HTLV III B.

Every three days the lymphocytes were taken up in a RPMI medium supplemented with 10% of foetal calf serum in a concentration of $3 \times 10^5$ cells/ml.

AY 9944, AZT or a mixture of AY 9944 and AZT were added to the medium.

After 30 days of culture, the presence of the virus was measured using a P24 test, cellular proliferation was measured by incorporation of tritiated thymidine, cellular viability was measured by the Trypan Blue exclusion test, and the percentage of CD4 molecules expressed by the cells was measured.

The results are shown in the table below: −v signifies "without virus" and +v signifies "with virus".

A great deal of synergy was observed from a dose of $3 \times 10^{-8}$ M for AY 9944 and 1 μg/ml for AZT while even at a dose of $3 \times 10^{-6}$ M AY 9944 alone had only a small effect (p24=70) and AZT at a dose of 1 μg/mol had no effect (p24>1000).

AY 9944 has a restorative effect on cellular proliferation inhibited by the virus.

There was also a reduction in cellular mortality (from 58% with 1 μg/ml of AZT alone to 11% on adding AY 9944 in a concentration of only $3 \times 10^{-8}$ M).

Finally, the CD4 phenotype was restored, increasing from 26% to 83%, a normal value, on adding AY 9944 in a concentration of $3 \times 10^{-8}$ M to AZT (1 μg/ml).

The results are shown in the table below which represents the cumulative effect of AZT and AY 9944 on HIV multiplication, its lytic effect on lymphocytes and the CD4 antigen expression. These results were obtained after four weeks of culture of H9 cells infected by isolate (HIV-1IIIB). The lymphocytes were passed every three days and seeded at a concentration of $3 \times 10^{-5}$/ml.

As the results in the table show, AZT at 10 μg/ml, which has an anti-viral effect (p24=0), also has a suppressor effect (anti-proliferant) on the cells of the immune cell line H9 as cellular proliferation is reduced to 28 000 cpm for AZT. Adding AY (line 6 of the table) to this concentration of AZT raises cell proliferation to 47 000 cpm. This shows the resorative effect of AY 9944 on cellular proliferation in contrast to the activity of a drug which has an anti-proliferative effect (AZT at 10 μg/ml).

|  | P 24 (pg/ml) | Proliferation (cpm) | Viability (% dead cells) | % CD4 |
|---|---|---|---|---|
| − v | 0 | 63000 | 9 | 82 |
| + v | 2500 | 2153 | 67 | 22 |
| + v (AZT 10 μg/ml) | 0 | 28136 | 11 | 83 |
| + v (AZT 1 μg/ml) | 1700 | 7199 | 58 | 26 |
| + v (AY 9944 $3.10^{-6}$ M) | 70 | 37620 | 14 | 87 |
| + v (AY 9944 $3.10^{-6}$ M; AZT 10 μg/ml) | 0 | 47049 | 11 | 80 |
| + v (AY 9944 $3.10^{-6}$ M; AZT 1 μg/ml) | 0 | 60254 | 10 | 78 |
| + v (AY 9944 $3.10^{-7}$ M; AZT 1 μg/ml) | 0 | 59000 | 9 | 79 |
| + v (AY 9944 $3.10^{-8}$ M; AZT 1 μg/ml) | 0 | 61000 | 11 | 83 |

Example 14

Tablets were prepared which had the formula:

| | |
|---|---|
| trans-1, 4-bis [2-chlorobenzylaminomethyl] cyclohexane dihydrochloride | 10 mg |
| excipient, q.s. for finished tablet, to (excipient details: lactose, starch, talc, magnesium stearate). | 100 mg |

Example 15

Sectile tablets were prepared with the following formula:

| | |
|---|---|
| trans-1, 4-bis [2-chlorobenzylaminomethyl] cyclohexane dihydrochloride | 15 mg |
| excipient, q.s. for finished tablet, to (excipient details: lactose, starch, talc, magnesium stearate). | 100 mg |

Example 16

Sectile tablets were prepared with the following formula:

| | |
|---|---|
| trans-1, 4-bis [2-chlorobenzylaminomethyl] cyclohexane dihydrochloride | 15 mg |
| AZT | 100 mg |
|  | 250 mg |
| excipient, q.s. for finished tablet, to (excipient details: lactose, starch, talc, magnesium stearate) | |

What is claimed is:

1. A method for the treatment of an iatrogenic disease, nosocomial-bacterial comprising administering orally or by injection to said patient an amount effective for said therapy of a compound of the formula

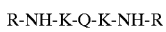 (I)

where Q represents a divalent radical with the following formulae II to V:

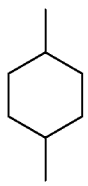 (II)

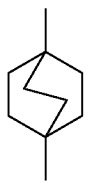 (III)

 (IV)

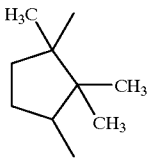 (V)

K represents a methylene group or, when the symbol Q is represented by formula II, a valence bond and the symbol R is a radical selected from the group formed by the following radicals VI to XVII:
VI Benzyl;
VII Benzyl substituted by one, two or three trihalomethyl groups;
VIII Substituted trihalomethyl benzyl;
IX Indanyl;
X Alkyl;
XI Cycloalkyl;
XII Cycloalkylalkyl;
XIII Alkenyl;
XIV Cycloalkenylalkyl;
XV Bicycloalkyl;
XVI Bicycloalkenylalkyl;
XII Bicycloalkylalkyl;
or an addition salt thereof with a mineral or organic acid.

2. A method according to claim 1 wherein said patient is suffering from an infection of iatrogenic origin, and said amount is sufficient for the treatment of said infection.

3. A method according to claim 1 further comprising also administering to said patient a second compound having antiviral properties.

4. A method according to claim 3 wherein said second compound having antiviral properties is selected from the group consisting of DDI, DDC, antiproteases, 3TC and AZT.

5. A method for the treatment of a viral infection in a patient in need of said therapy, comprising administering to said patient an amount sufficient to treat said viral infection of a compound of the formula:

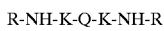 (I)

where Q represents a divalent radical with the following formulae II to V:

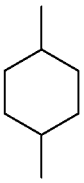 (II)

 (III)

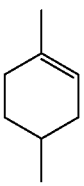 (IV)

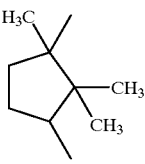 (V)

K represents a methylene group or, when the symbol Q is represented by formula II, a valence bond and the symbol R is a radical selected from the group formed by the following radicals VI to XVII:
VI Benzyl;
VII Benzyl substituted by one, two or three trihalomethyl groups;
VIII Substituted trihalomethyl benzyl;
IX Indanyl;
X Alkyl;
XI Cycloalkyl;
XII Cycloalkylalkyl;
XIII Alkenyl;
XIV Cycloalkenylalkyl;
XV Bicycloalkyl;
XVI Bicycloalkenylalkyl;
XII Bicycloalkylalkyl;
or an addition salt thereof with a mineral or organic acid.

6. A method for the treatment of a parasitic infection in a patient in need of said therapy, comprising administering to said patient an amount sufficient to treat said parasitic infection of a compound of the formula

R-NH-K-Q-K-NH-R (I)

where Q represents a divalent radical with the following formulae II to V:

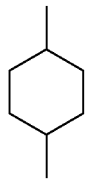
(II)

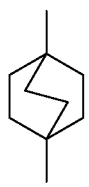
(III)

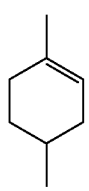
(IV)

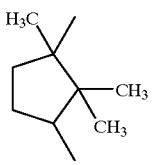
(V)

K represents a methylene group or, when the symbol Q is represented by formula II, a valence bond and the symbol R is a radical selected from the group formed by the following radicals VI to XVII:
VI Benzyl;
VII Benzyl substituted by one, two or three trihalomethyl groups;
VIII Substituted trihalomethyl benzyl;
IX Indanyl;
X Alkyl;
XI Cycloalkyl;
XII Cycloalkylalkyl;
XIII Alkenyl;
XIV Cycloalkenylalkyl;
XV Bicycloalkyl;
XVI Bicycloalkenylalkyl;
XII Bicycloalkylalkyl;
or an addition salt thereof with a mineral or organic acid.

7. A method for the treatment of a tumor in a patient in need of said therapy, comprising administering to said patient an amount sufficient to treat said tumor of a compound of the formula

R-NH-K-Q-K-NH-R (I)

where Q represents a divalent radical with the following formulae II to V:

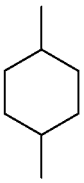
(II)

(III)

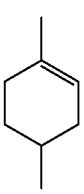
(IV)

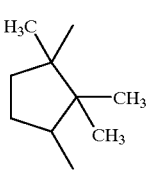
(V)

K represents a methylene group or, when the symbol Q is represented by formula II, a valence bond and the symbol R is a radical selected from the group formed by the following radicals VI to XVII:
VI Benzyl;
VII Benzyl substituted by one, two or three trihalomethyl groups;
VIII Substituted trihalomethyl benzyl;
IX Indanyl;
X Alkyl;
XI Cycloalkyl;
XII Cycloalkylalkyl;
XIII Alkenyl;
XIV Cycloalkenylalkyl;
XV Bicycloalkyl;
XVI Bicycloalkenylalkyl;
XII Bicycloalkylalkyl;
or an addition salt thereof with a mineral or organic acid.

8. A method for producing an immunomodulating effect in a patient in need thereof, comprising:

administering to said patient an amount effective for producing an immunomodulating effect of a compound of the formula

R-NH-K-Q-K-NH-R (I)

wherein Q represents a divalent radical with the following formulae II to V:

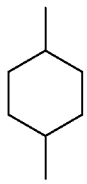

(II)

(III)

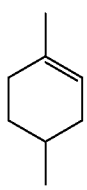

(IV)

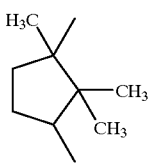

(V)

K represents a methylene group or, when the symbol Q is represented by formula II, a valence bond and the symbol R is a radical selected from the group formed by the following radicals IV to XVII:
VI Benzyl;
VII Benzyl substituted by one, two or three trihalomethyl groups;
VIII Substituted trihalomethyl benzyl;
IX Indanyl;
X Alkyl;
XI Cycloalkyl;
XII Cycloalkylalkyl;
XIII Alkenyl;
XIV Cycloalkenylalkyl;
XV Bicycloalkyl;
XVI Bicycloalkenylalkyl;
XII Bicycloalkylalkyl;
or an addition salt thereof with a mineral or organic acid.

9. A method according to claim 8 wherein said patient is a patient in need of restoration of expression of at least one of said patient's (1) cytokine genes or (2) cytokine gene receptors.

10. A method according to claim 8 wherein said patient is a patient in need of stimulation of the production of inflammatory molecules.

11. The method according to claim 10 wherein said patient is a patient in need of stimulation of the production of chimiokines.

12. A method according to claim 8 wherein said patient is a patient who has an iatrogenic disease induced by the action of at least one of an immunosuppressor or a corticoid.

13. A method for the treatment of an autoimmune disease in a patient in need of said therapy, comprising:

administering to said patient and amount sufficient to treat said autoimmune disease of a compound of the formula

R-NH-K-Q-K-NH-R (I)

wherein Q represents a divalent radical with the following formulae II to V:

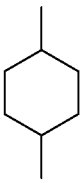

(II)

(III)

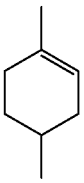

(IV)

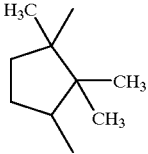

(V)

K represents a methylene group or, when the symbol Q is represented by formula II, a valence bond and the symbol R is a radical selected from the group formed by the following radicals IV to XVII:
VI Benzyl;
VII Benzyl substituted by one, two or three trihalomethyl groups;
VIII Substituted trihalomethyl benzyl;
IX Indanyl;
X Alkyl;

XI Cycloalkyl;
XII Cycloalkylalkyl;
XIII Alkenyl;
XIV Cycloalkenylalkyl;
XV Bicycloalkyl;
XVI Bicycloalkenylalkyl;
XII Bicycloalkylalkyl;

or an addition salt thereof with a mineral or organic acid.

14. A method according to claim 13 wherein said patient is a patient who has an autoimmune disease of rheumatoid polyarthritis, lupus erythematosus or autoimmune diabetes, and said amount administered is sufficient to treat said autoimmune disease.

* * * * *